(12) United States Patent
D'Agosto

(10) Patent No.: US 6,976,491 B2
(45) Date of Patent: Dec. 20, 2005

(54) GAG-LESS AIRWAY FOR SNORING PREVENTION

(76) Inventor: Joseph D'Agosto, 95 Fitch Ave., Darien, CT (US) 06820

( * ) Notice: Subject to any disclaimer, the term of this patent is extended or adjusted under 35 U.S.C. 154(b) by 179 days.

(21) Appl. No.: 10/697,177

(22) Filed: Oct. 30, 2003

(65) Prior Publication Data

US 2005/0092331 A1 May 5, 2005

(51) Int. Cl.[7] .................................................. A61C 5/14
(52) U.S. Cl. ..................... 128/859; 128/200.24; 482/13
(58) Field of Search ................. 128/859, 848, 128/860, 861, 206.29, 200.26, 201.26, 201.11, 128/200.24; 602/902; 2/182.6; 433/140; 600/590; 604/77; D24/136; 482/13

(56) References Cited

U.S. PATENT DOCUMENTS

| | | | | |
|---|---|---|---|---|
| 4,425,911 A | * | 1/1984 | Luomanen et al. | 128/200.26 |
| 4,676,240 A | * | 6/1987 | Gardy | 128/848 |
| 5,154,184 A | * | 10/1992 | Alvarez | 128/848 |
| 5,915,385 A | * | 6/1999 | Hakimi | 128/848 |
| 5,921,241 A | * | 7/1999 | Belfer | 128/848 |

* cited by examiner

*Primary Examiner*—Henry Bennett
*Assistant Examiner*—Shumaya B. Ali
(74) *Attorney, Agent, or Firm*—Alfred E. Miller

(57) ABSTRACT

An oral application for snoring prevention which has a flattened tube with an unobstructed airway and ridges on the inferior surface for pulling the tongue forward out of the path of the airway while the superior surface of the tube follows closely the hard and soft palate. The tube is short and extends in the oral cavity or mouth to a location which will not cause a gag reflex.

5 Claims, 4 Drawing Sheets

GAG-LESS AIRWAY FOR SNORING PREVENTION

The present invention relates to an oral appliance that fits within the mouth and is worn at night upon retiring, and which maintains the tongue interiorly without causing the person to gag while sleeping.

It is known that snoring occurs when there is a partial obstruction of the free flow of air in the passages at the back of the mouth and the nose. The area is a collapsible airway where the tongue falls back on the soft palate and the pharynx. During sleep the throat muscles relax causing the tissues to sag whereby the breathing passage is narrowed. Consequently, the air moving faster through the smaller space causes the tissues to vibrate resulting in snoring.

There are many devices and appliances to prevent snoring. One of these devices is an appliance, such as a mouthpiece that holds the lower jaw forwardly during sleep, which is designed to open the airway in the throat. These devices are uncomfortable resulting in stiffness of the jaw when waking up. A device for reducing snoring is shown and described in U.S. Pat. No. 4,676,240 to Gardy which is a bulky appliance that is worn in the user's mouth and has a tongue receiving chamber for holding the tongue forward and which has parallel through holes that permit air flow through the mouth while a vacuum created in the tongue chamber resists the rearward pull of the tongue when the user falls asleep. The device is uncomfortable because of its bulk and depends upon creating a vacuum in the tongue chamber sufficient to resist the rearward pull of the tongue.

There are also other devices, such as the Rusch oral airway used by medical practitioners to maintain an airway in an open condition. These airways are tubular and curved and provided with a mouthpiece. The oral airways presently available are of such a configuration and length that they push the tongue forward, thus requiring an anesthetized patient since they cause a gag reflex elicited by stimulating the posterior one third in the back of the oral cavity.

SUMMARY OF THE INVENTION

It is a feature of the present invention to provide an airway, unlike the medical airway described above which is larger in circumference but shorter in length then the medical airway, and that is constructed in a way to prevent snoring by a sleeping individual.

It is another feature of the present invention in which the gag-less oral airway is a somewhat flattened tube that is shorter in length than the present tubular airway that does not push the tongue forward as known devices, but instead pulls the tongue forward by traction ridges or saw like notches on the inferior surface of the tube while the superior surface of the tube has a dedicated contour to the hard palate of the user's mouth.

The airway is provided with a flange at the forward end of the tube as prevention against swallowing by the user. The airway and flange are also provided with spaced openings in the opposite sides of the tube so that there is free passage of air into the user's mouth regardless of the position of the adult anti-snoring pacifier in the mouth. The tube is composed of a relatively soft elastomeric material so as not to damage the oral mucosa, tongue or teeth of the user.

The above and other features of the present invention will be apparent by reference to the following description of my invention together with the drawings.

DESCRIPTION OF THE PREFERRED EMBODIMENT

Figure 1:
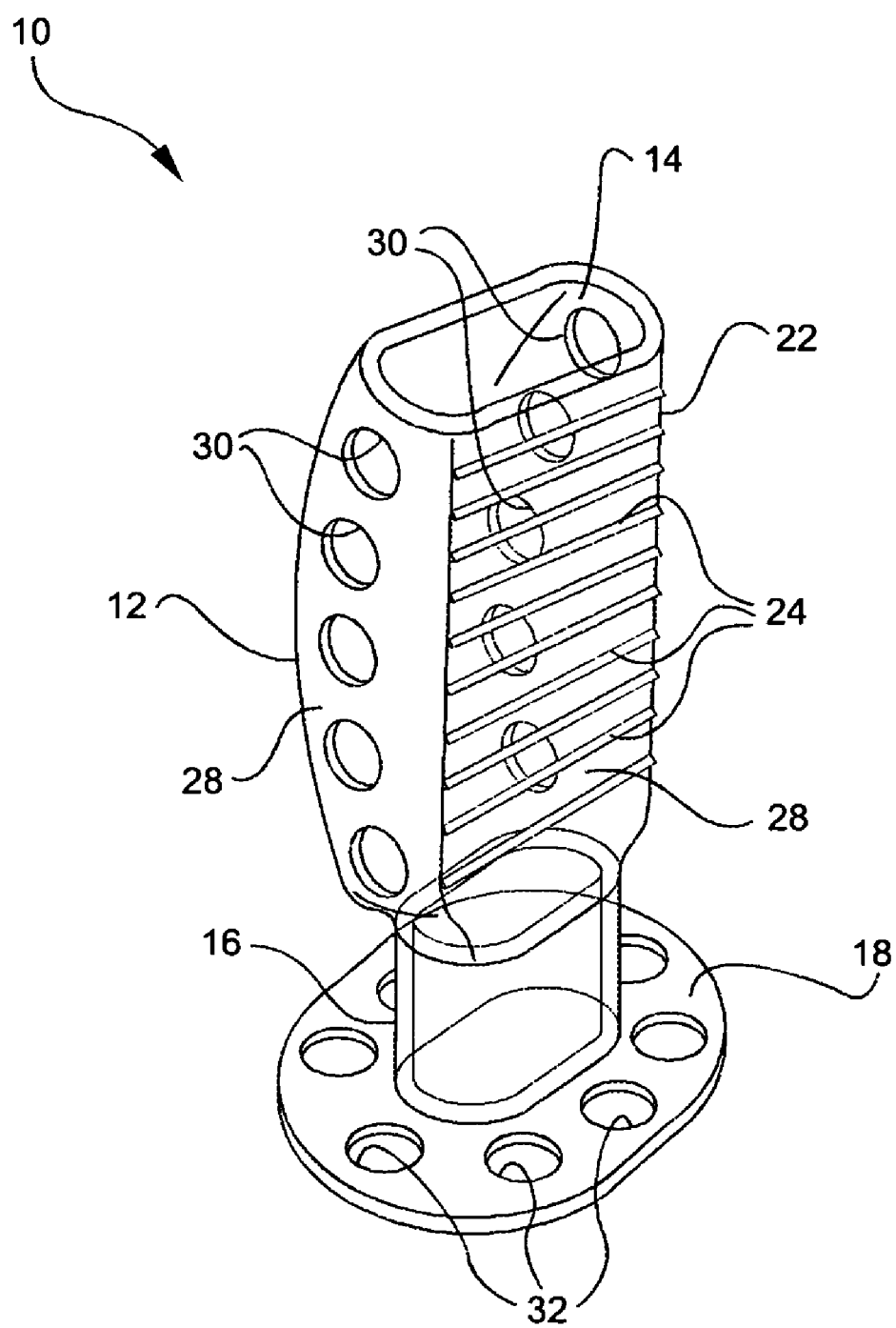
FIG. 1 is a perspective view of the airway device constructed in accordance with the teachings of the present invention.
Figure 2:
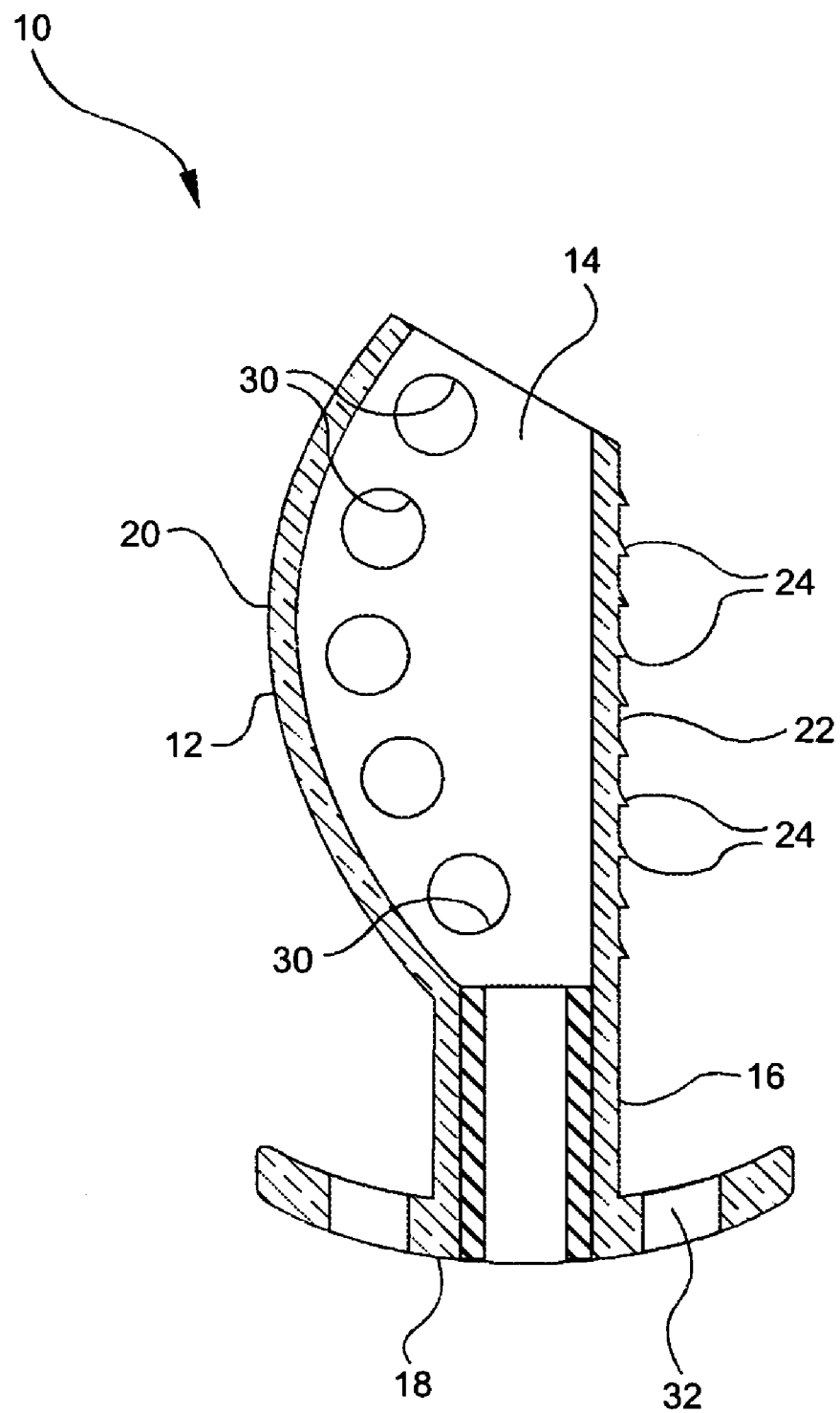
FIG. 2 is a cross-sectional view of the airway device shown in FIG. 1.

Referring to FIGS. 1 and 2 of the drawings, an anti-snoring oral appliance is shown as an airway referred to by the reference numeral 10 which is shaped as a flattened tube 12 with a through channel or unobstructed airway 14 for the passage of air. The flattened tube 12 has an increased diameter, as seen in FIG. 1. The forward end 16 of the tube is provided with a flange 18 that is positioned substantially perpendicular to the forward end 16 of the tube. The tube has a tap surface 20. In fact, the present device can be characterized as an adult anti-snoring pacifier.

It should be noted that the length of the tube 14 has been carefully chosen so that the superior surface closely follows the contour of the hard palate, and extends only into the anterior two thirds of the user's oral cavity, and the end remote from the flange terminates at the junction of the hard and soft palate. Consequently, the adult pacifier will not reach the sensitive area in the back of the oral cavity, or throat, which causes the gag reflex. Thus, the user of the present anti-snoring device can sleep comfortably without gagging.

Located on the bottom surface 22 of the airway tube are a series of spaced traction ridges 24 which pulls the tongue 26 forward in order to decrease obstructions to the users's airway channel and also functions as an aid in reducing snoring. In addition, the saw-like traction ridges 24 on the bottom of the flattened tube are so shaped and angled that they grab a greater surface of the tongue and they not only pull the tongue forward in the mouth but they also maintain the tongue in the forward position to keep it from falling back into obstructing the airway.

Opposite sides 28 of the flattened tube 12 are provided with spaced openings 30 and the flange 18 has spaced openings 32, as well. These openings, or perforations, permit the passage of air into the oral cavity regardless of the position of the airway in the user's mouth.

The adult anti-snoring pacifier of the present invention is fabricated of a soft elastomeric material such as silicone, polyethylene or polypropylene so that when used it will not damage the oral mucosa, tongue or teeth.

Figure 3:
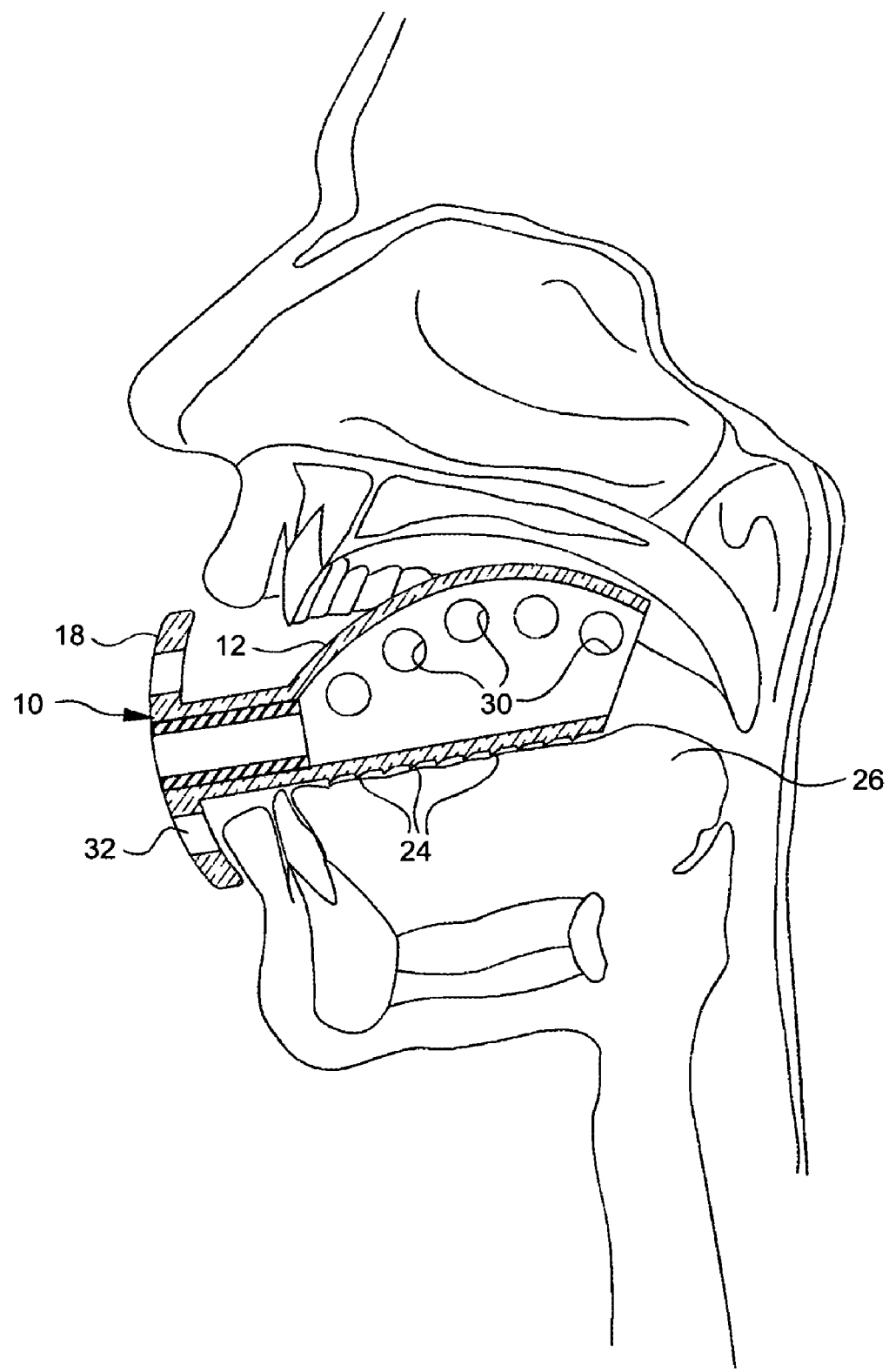
FIG. 3 is a sectional view of the airway device of the present invention being partially inserted in the user's mouth and FIG. 4 is a sectional view of the airway device of the present invention fully inserted in the mouth showing the airflow through the channel and openings in the tube and flange for unrestricted airflow, which functions as an anti-snoring appliance.
Figure 4:
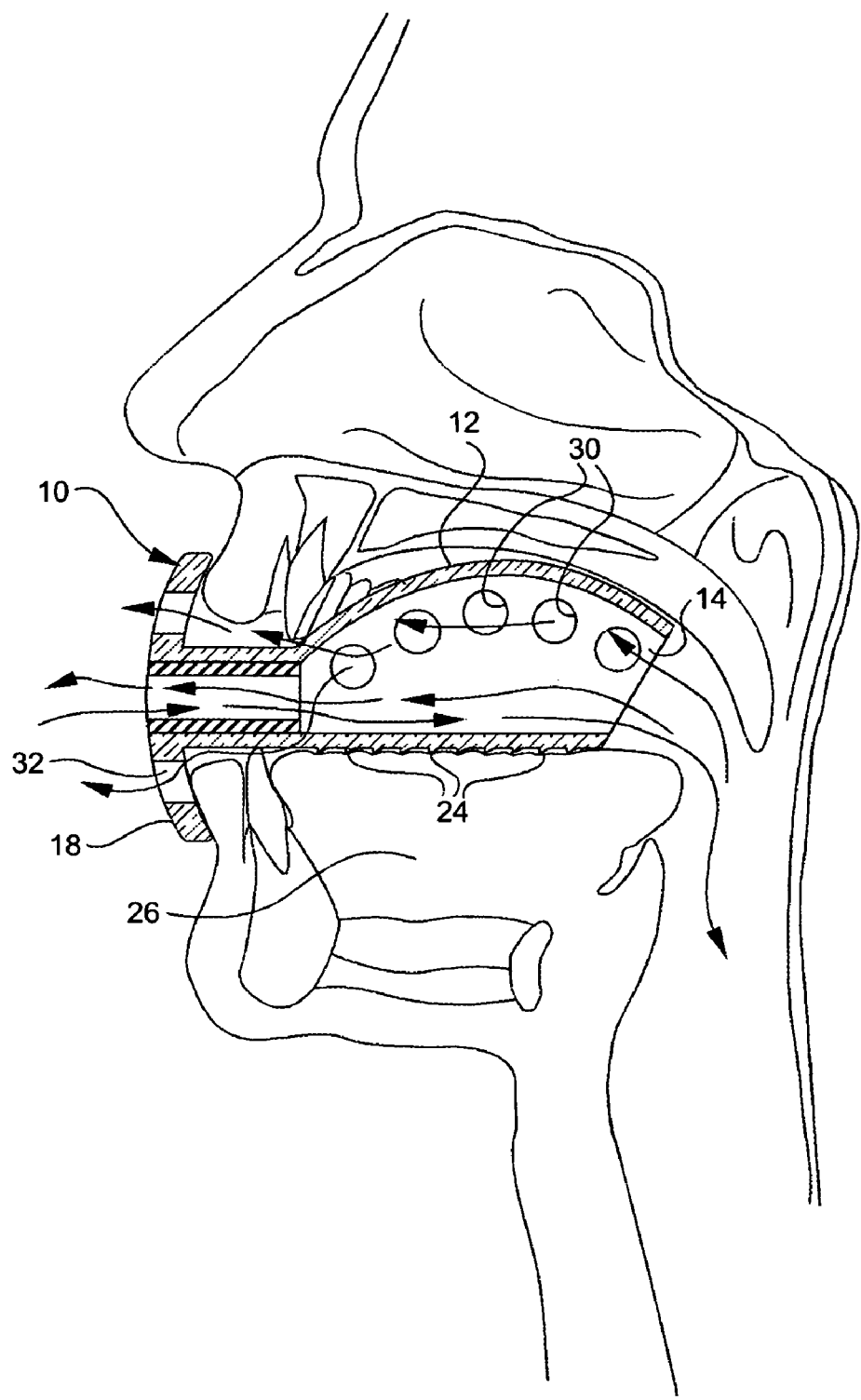

Referring now to FIGS. 3 and 4, the present appliance is shown in FIG. 3 being partially inserted in the user's mouth with the saw-like ridges 24 engaging the tongue in a manner to pull the tongue forward, and when the appliance is fully inserted in the mouth, as seen in FIG. 4, the tongue does not impede the air passage thus permitting the free flow of air during inhalation and exhalation while sleeping.

The present anti-snoring adult pacifier, has a relatively short length which ensures that the user will not gag by not reaching the sensitive area in the back of the throat, and pulls the tongue out of the airway blocking position.

While the present invention has been disclosed and described with reference to a single embodiment, it will be apparent that changes and modifications may be made therein, and it is intended in the following claims to cover each variation and modification as falls within the true spirit and scope of the invention.

What is claimed is:

1. A gag-less airway device for inserting in the user's mouth comprising a flattened tube open on both ends having an unobstructed airway, said tube being of such a length that it will not simulate the gag reflex in the user when the device is inserted in the oral cavity, the top surface of said tube closely following the contour of the hard palate of the mouth, a bottom surface of said tube having substantially parallel ridges which are traction means for engaging and pulling the user's tongue forward upon insertion of the device in the mouth, and a flange at a forward end of said device located substantially perpendicular to said flattened tube.

2. A gag-less airway as claimed in claim 1 wherein the length of the device only extends through the anterior two thirds of the oral cavity.

3. A gag-less airway device as claimed in claim 1 wherein said airway is composed of a soft elastomeric material.

4. A gag-less airway device as claimed in claim 1 wherein at least one side of said tube is provided with a plurality of openings for the passage of air there through.

5. A gag-less airway device as claimed in claim 1 whereby said flange is provided with spaced openings.

* * * * *